(12) United States Patent
Marquez Alvarez

(10) Patent No.: US 8,012,156 B2
(45) Date of Patent: Sep. 6, 2011

(54) INTERSOMATIC CAGE, CLAMP FOR MANIPULATING IT AND PROCEDURE FOR INSERTING THE INTERSOMATIC CAGE BETWEEN VERTEBRAE

(75) Inventor: Luis Marquez Alvarez, Reus Tarragona (ES)

(73) Assignee: Traiber, S.A., Reus Tarragona (ES)

( * ) Notice: Subject to any disclaimer, the term of this patent is extended or adjusted under 35 U.S.C. 154(b) by 492 days.

(21) Appl. No.: 11/602,171

(22) Filed: Nov. 17, 2006

(65) Prior Publication Data

US 2008/0119935 A1   May 22, 2008

(51) Int. Cl.
*A61B 17/70* (2006.01)
*A61F 2/44* (2006.01)

(52) U.S. Cl. .................. 606/99; 606/86 A; 623/17.11; 623/17.16

(58) Field of Classification Search .......... 606/205–211, 606/99, 86 A; 623/17.11–17.16, 908
See application file for complete search history.

(56) References Cited

U.S. PATENT DOCUMENTS

| 2002/0072752 A1* | 6/2002 | Zucherman et al. ............ 606/99 |
| 2004/0172130 A1* | 9/2004 | Nakahara et al. .......... 623/17.11 |
| 2005/0125062 A1* | 6/2005 | Biedermann et al. ....... 623/17.11 |
| 2005/0131542 A1* | 6/2005 | Benzel et al. .............. 623/17.13 |
| 2005/0240267 A1* | 10/2005 | Randall et al. ............. 623/17.11 |
| 2006/0200247 A1* | 9/2006 | Charrois .................... 623/19.11 |
| 2007/0142843 A1* | 6/2007 | Dye ............................... 606/99 |
| 2008/0077153 A1* | 3/2008 | Pernsteiner et al. ............ 606/99 |
| 2008/0097454 A1* | 4/2008 | DeRidder et al. ............... 606/99 |

FOREIGN PATENT DOCUMENTS

EP       1 290 985 A2   3/2003

* cited by examiner

*Primary Examiner* — Thomas C. Barrett
*Assistant Examiner* — Michael T Schaper
(74) *Attorney, Agent, or Firm* — Knobbe Martens Olson & Bear LLP

(57) ABSTRACT

The invention relates to an intersomatic cage for intervertebral inclusion and fixing of said vertebrae, provided on its side face with at least one orifice or recess allowing it to be held by the holding clamp; this clamp is provided with hinged arms that can slide relative to one another, their sliding motion being controlled from their rear. The clamp body includes a copying device that reproduces at all times the position of the intersomatic cage as it is held by the clamp, always showing its intervertebral location. The invention is completed by the procedure for placing the intersomatic cages between the vertebrae.

15 Claims, 4 Drawing Sheets

INTERSOMATIC CAGE, CLAMP FOR MANIPULATING IT AND PROCEDURE FOR INSERTING THE INTERSOMATIC CAGE BETWEEN VERTEBRAE

OBJECT OF THE INVENTION

The object of the invention relates to the field of intervertebral implants as complements for the immobilisation of two adjacent vertebrae by inserting an intersomatic cage between them.

These implants are placed between two vertebrae when the intervertebral disc has degenerated, with the ensuing approach of the vertebrae and the local compression of the spinal cord and the nerve roots that arise from it.

BACKGROUND OF THE INVENTION

Intervertebral implants using an intersomatic cage are known in the state of the art, adopting several preferred embodiments, and are an efficient method for separating the vertebrae when the intervertebral disc has worn out.

Operations of this type involve removing the intervertebral disc and replacing it with a piece known as the intersomatic cage, which maintains the intervertebral separation, thereby preventing the compression of the spinal cord and the nerves that arise from it. To allow the attachment of the intersomatic cage on the vertebrae, the cage is designed with a toothing on its upper and lower surfaces, that is, those that are in contact with the vertebrae, which will be attached to the vertebra to prevent the relative displacement of the vertebra and the intersomatic cage.

Spanish Patent ES-2,211,253, which is known in the state of the art, relates to an intersomatic cage with side openings that allow a radiological monitoring of bone growth and a through vertical orifice that conforms an inner space in which the bone insert is housed. It is provided on its top and bottom with serrated teeth that increase its grip on the adjacent vertebrae. A problem with cages of this type is their positioning, as they are introduced between the vertebrae in a straight manner, so that the teeth prevent an easy entry of the cage. Thus, the cage must be placed by hammering, with the ensuing inconvenience to the patient.

An additional drawback of intersomatic cages of the state of the art is that their position cannot be modified at all if necessary, as the system is irreversible.

Yet another drawback to the state of the art is the continued exposure to X-rays needed to constantly monitor the positioning of these intersomatic cages.

DESCRIPTION OF THE INVENTION

The present invention intends and manages to overcome the drawbacks listed in the prior art section. For this purpose, the first object of the invention is an improved intersomatic cage.

Another object of the invention is the clamp for inserting the said intersomatic cage in the intervertebral cavity, which allows the cage to be held firmly and a rotational movement to be produced for an intervertebral insertion that is less invasive than the conventional method.

Also the object of this invention is to know at all times the position of the intersomatic cage in the intervertebral cavity without requiring X-rays.

Lastly, another object of the invention is the procedure for inserting the intersomatic cage in its intervertebral space, controlling at all times the positioning and attachment and even controlling the possibility of extraction, which allows a reversible movement. This rotational insertion and extraction movement is not performed by any other currently known system.

As regards the description of the intersomatic cage, firstly it must be pointed out that its side surface is provided with at least one orifice or notch, through or blind, the side surface of the cage preferably having at least two orifices or notches, the purpose of which is to provide attachment points for the positioning clamp that will be described further below.

These orifices or notches have a rounded or circular configuration, into which the protruding ends of the clamp fit. These orifices or notches may have tronco-conical outer ends that facilitate the movement between the clamp arms and the intersomatic cage.

The presence of these orifices will allow the clamp to hold the intersomatic cage during its insertion between the vertebrae, preventing the risk of the cage being released.

Similarly, the intersomatic cages are provided on their upper and lower surfaces with corresponding parallel toothings, straight or curved, that allow the cage to grip the vertebrae. The purpose of the curve is to facilitate the rotation effected during the insertion of the intersomatic cage in the intervertebral space. In this case the teething profile does not require flattening the tooth points, defining toothed profiles similar on both edges on both surfaces, as this will not prevent retracting the intersomatic cage since as it turns it will follow the normal profile of the toothing, but will prevent to a great extent any displacement of the joined vertebrae.

A second object of the invention is in the clamp used to hold and insert the intersomatic cages in the intervertebral space. This clamp is constituted by two arms hinged at a central point, the hinge allowing the relative displacement of the arms. When holding the intersomatic cage with the movable clamp ends this relative displacement of the arms will allow the cage to turn on the axis by which it is held, with this rotation movement positioning it in the intervertebral space.

The posterior ends of the clamp have a device for adjusting the displacement of the clamp arms. In essence, this device consists of a screw threaded on one of the arms of the clamp, a counter placed actuation handle for said screw and an intermediate recessed area in which is introduced the other arm of the clamp, with a channel-like shape that fits in the recessed portion of the actuation device. Therefore, turning the adjustment device in either direction will slide the two arms of the clamp body.

The clamp is completed by a copying element that reproduces the shape and position in which the intersomatic cage is held by the clamp. This copying element is joined by its central position to one of the arms of the clamp, allowing a turning motion while on the periphery of the copying element is hinged together an arm that is attached to the other arm of the clamp, reproducing in the copying element a turn identical to that produced by the intersomatic cage held by the clamp ends. When the clamp arms slide against each other the intersomatic cage will turn, thereby turning the copying element, externally reproducing the situation of the intersomatic cage between the vertebrae to allow the surgeon to know its position, as the cage is not visible during the operation. This device is extremely useful as it renders unnecessary the execution of multiple X-rays of the area to view the position of the cage, with the resulting risk of X-ray exposure.

The procedure for attaching the intersomatic cage is also an object of the invention. It comprises of the following operations:

Adjusting the terminal ends of the clamp on the corresponding orifice(s) or recess(es) of the intersomatic cage;

Tightening the clamp arms and holding the intersomatic cage firmly;

Bringing the clamp ends closer until they are between the vertebrae in which the intersomatic cage will be introduced;

Sliding of the clamp arms against each other using a posterior actuator, with the resulting hinged rotation of the intersomatic cage and the rotation of the copying element to reproduce the rotation of the intersomatic cage;

Placing the intersomatic cage in the intervertebral cavity;

Opening and removing the clamp.

BRIEF DESCRIPTION OF THE DRAWINGS

To complete the description being made and in order to aid a better understanding of the characteristics of the invention, the present descriptive memory is accompanied by a set of drawings where, for purposes of illustration only and in a non limiting sense, the following is shown.

DESCRIPTION OF A PREFERRED EMBODIMENT OF THE INVENTION

Figure 1:
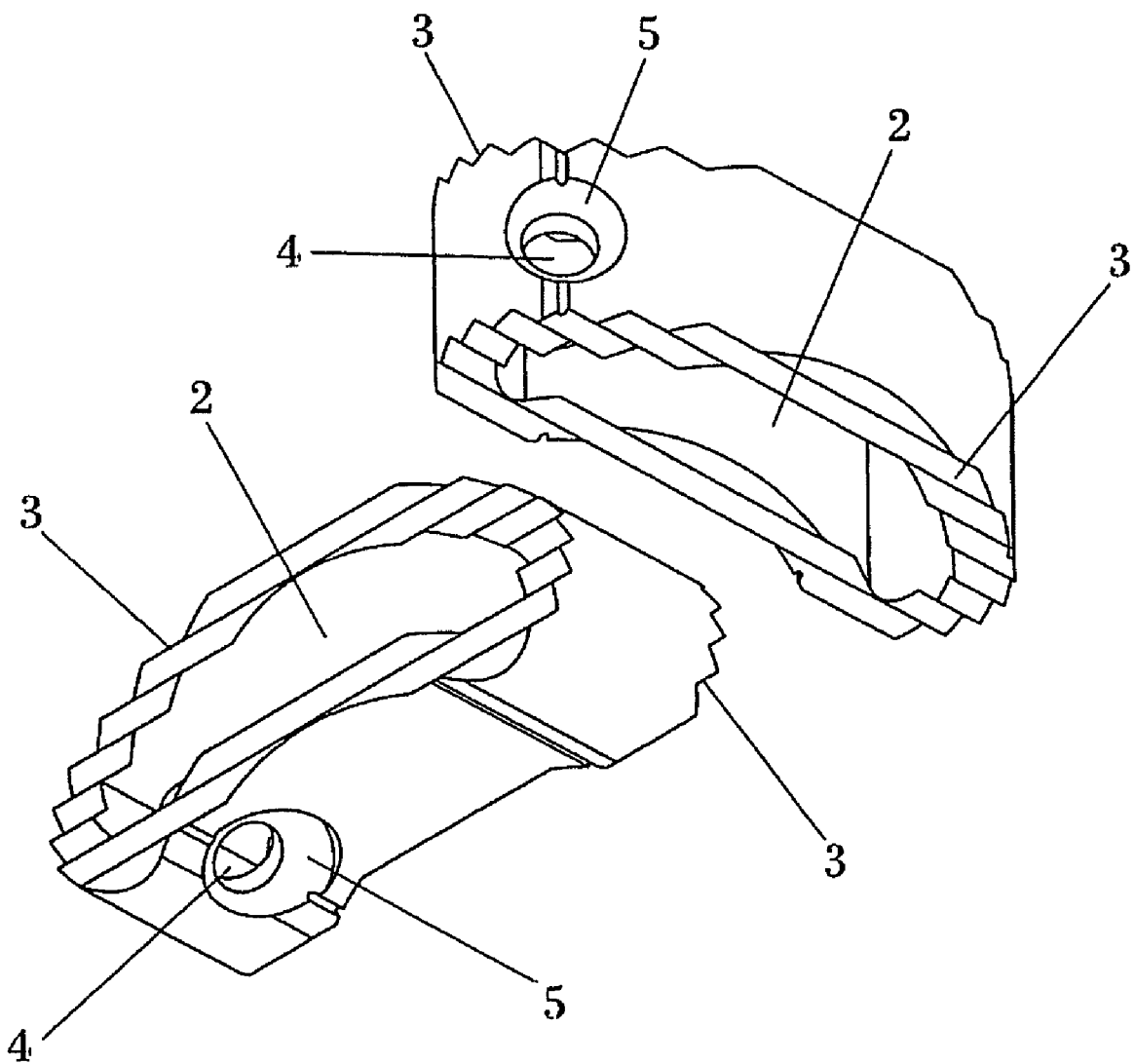
FIG. 1 shows a perspective view from several angles of an intersomatic cage including the improvements of the invention.

FIG. 1 shows a perspective view of an intersomatic cage (1) that includes the improvements of the invention. In this example, the cage has a lobular shape with a central space (2) and both the upper and lower surfaces, which will be in contact with the vertebrae, are provided with straight or curved toothings with a serrated structure that will engage the vertebrae to prevent their relative displacement.

Figure 3:
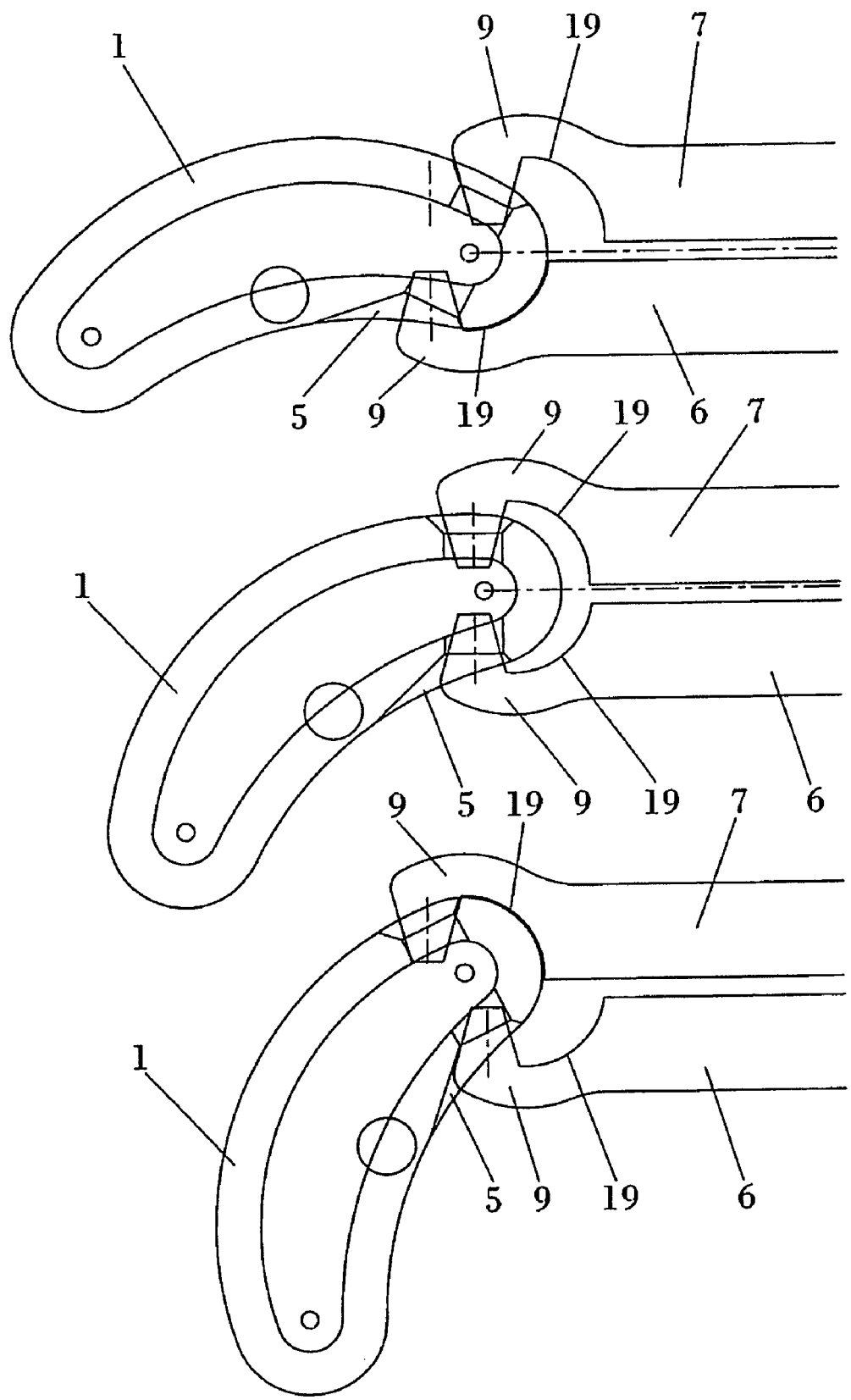
FIG. 3 shows three sequential views of the movement of the ends of the clamp and the displacement of the intersomatic cage.

One area of the side wall, and optionally the opposite position as well, has an orifice or recess (4) that can reach the hollow central area (2), which may be limited externally by a troncoconical recess (5) as shown in the sequential figures of FIG. 3, in which the relative position of the ends of the clamp and the intersomatic cage require said troncoconical recess (5) to allow the free range of motion in the rotation of the intersomatic cage.

Figure 2:
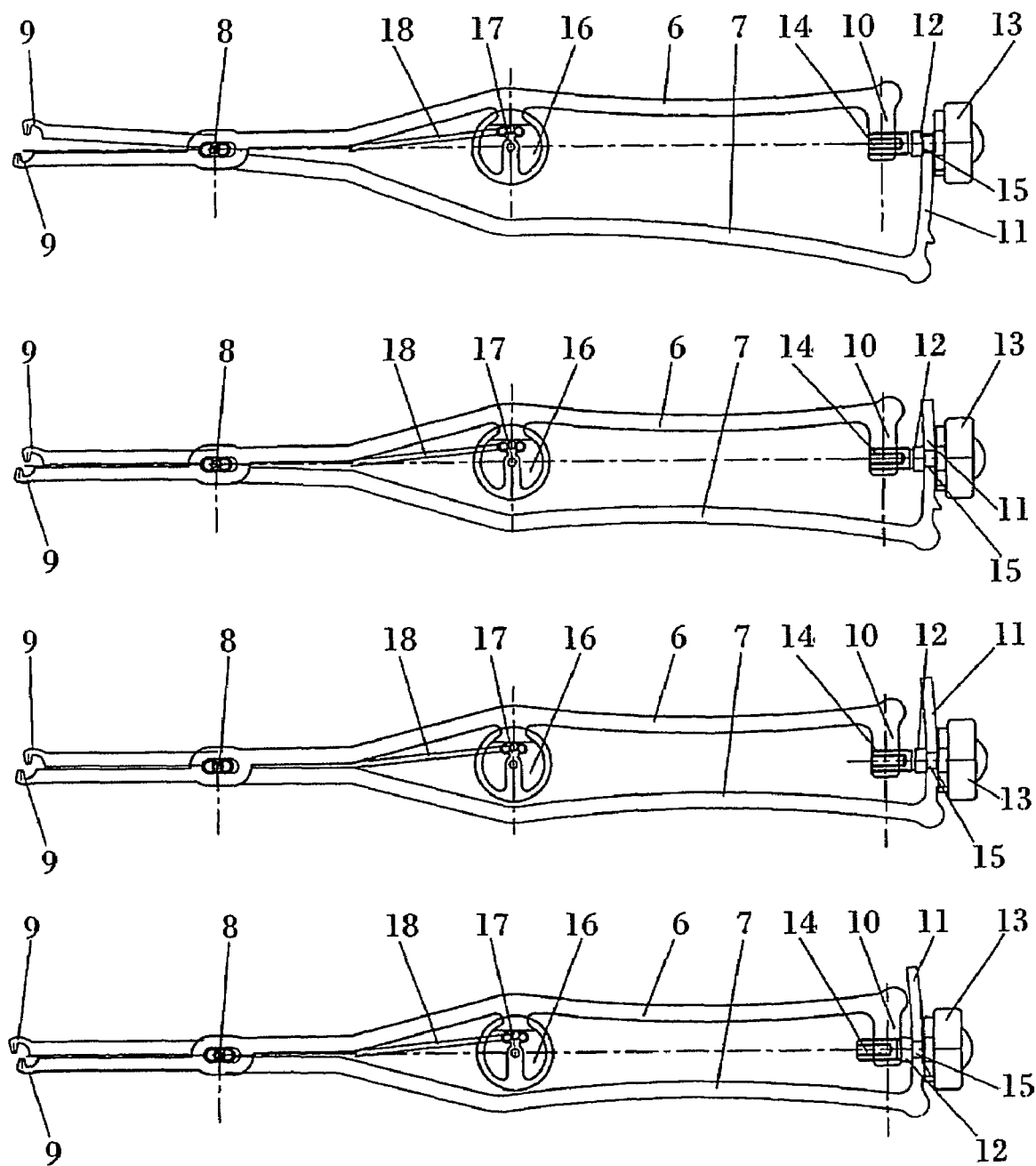
FIG. 2 shows four upper views of the clamp of the invention in the operation sequence. The clamp arms hold the intersomatic cage by pressing them together until they click. At this time the intersomatic cage is perfectly clamped so that, even if the clamp is released, it will continue to hold the intersomatic cage. This is, it seizes the intersomatic cage and holds it.

FIG. 2 shows in four sequences the relative motion of the arms of the clamp (6) (7), which are centrally joined in the sliding union (8) formed by a shaft that slides in a slanted groove, each of these elements belonging to each of the arms of the clamp, so that a relative displacement thereof will cause the clamp arms to slide against each other.

The anterior end (9) of the clamp arms is adapted for insertion in the orifices or recesses (4). The rear end of the clamp arms is arched at a pronounced angle, to define corresponding ends (10) and (11). Threaded at (14) the end (10) is a shaft (12) that regulates the axial sliding between arms, ending at the actuation wheel (13), while at its intermediate area said regulator shaft has a recess (15) inside which is held the end of the arm (11) with a fluted shape. This fluted shape of the end of the clamp arm (11) allows the free opening and closing motion of the clamp, while the axial sliding of the arms is conditioned by the position of the screw (12).

The copying device (16) is incorporated on one of the arms of the clamp (6) and is attached so that it may rotate around the shaft (17), while joined to the periphery of the copying device (16) is a cam (18) supported by the other arm of the clamp (7). The mutual sliding of the two arms of the clamp will make the copying device turn, and as its representation is similar to that of the position of the intersomatic cage between the ends of the clamp, the surgeon will have accurate information at all times on the position of said cage between the vertebrae, thereby avoiding the continuous exposure to X-rays required in conventional operations in which information on the position of the intersomatic cage is not available.

The copying device (16) has a screw-drive regulation (not shown in the figures) which allows adjusting this device to place it in the same position in which the intersomatic cage is held. The cam (18), in addition to a driving element of the copying device, is constituted as a spring for opening and closing the clamp.

Flexing the clamp will provide a constant tightening of the intersomatic cage even if the pressure normally exerted on the clamp arms is released.

The design of the clamp is such that it can be fully disassembled without any tools, to facilitate its cleaning.

Lastly, the system allows repositioning the intersomatic cage at any moment of the implanting process.

FIG. 3 includes three representations showing how the relative sliding of the ends (9) of the arms of the clamp (6) (7) causes the rotation of the intersomatic cage (1). For this purpose, the ends of the clamp have recesses (19) in which fit the sides of the cages, defining the end positions in which the aforementioned intersomatic cage is held.

Figure 4:
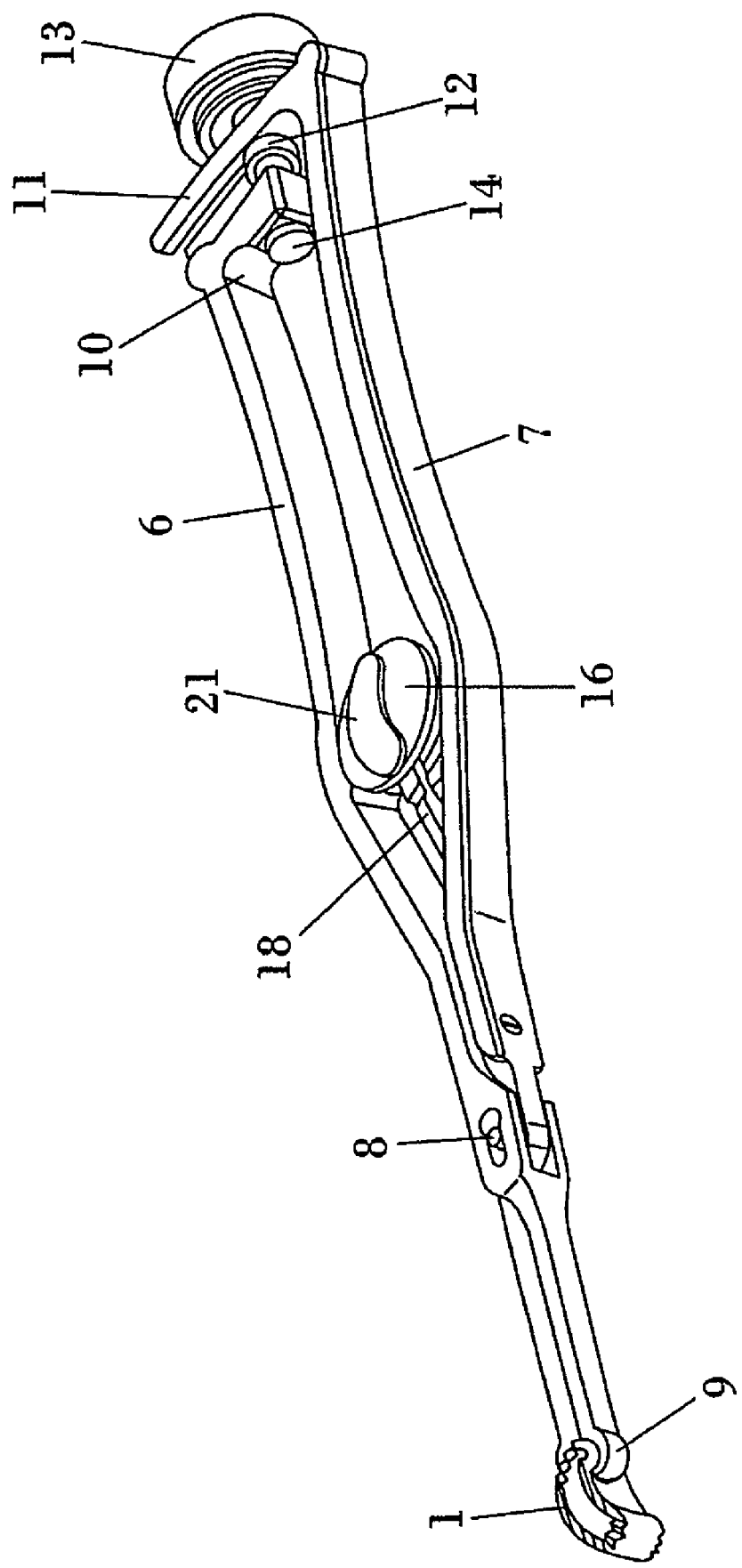
FIG. 4 shows a perspective view of the clamp holding an intersomatic cage.

FIG. 4 represents a perspective view of the clamp (20) holding the intersomatic cage (1). This figure shows the arms (6) and (7) holding the intersomatic cage by their ends (9) and how the shaft that joins the arms (6) and (7) constitutes a sliding union (8). Noteworthy in this figure is the copying device (16) with the upper shape (21) emulating the position of the intersomatic cage, and how this copying device (16) is guided by the action of a cam (18).

What is claimed is:

1. A system for intervertebral implantation comprising:
   an intersomatic cage which comprises at least one orifice made in the end of a cage lateral area, allowing it to be held by a clamp and positioned, said cage comprising two vertebral facing sides; and
   a clamp for manipulating said intersomatic cage, said clamp comprising
      two arms comprising an anterior end and a posterior end, said arms being crossed and hinged to each other at a central area by a hinge, said hinge allowing the arms to slide relative to each other; and
      a posterior attachment of said hinged arms that allows a free opening and closing motion and the regulated sliding motion of said arms;
      wherein said anterior end of said clamp arms comprises a shape adapted to at least one orifice used to hold said intersomatic cage;
      wherein said clamp further comprises a copying element that reproduces the shape and attachment rotational orientation of the intersomatic cage held by the clamp, this copying element being rotationally joined at a central area to one of the clamp arms, while hinged to the periphery of the copying element is a cam that is attached to the other clamp arm, reproducing in the copying element a rotation identical to that effected by the intersomatic cage held by the clamp ends.

2. The system for intervertebral implantation according to claim 1, wherein said cage comprises two orifices made in the end of the cage lateral area, allowing it to be held by said clamp and positioned.

3. The system for intervertebral implantation according to claim 2, wherein said two orifices are placed on opposite sides of the cage allowing it to be held by said clamp and positioned.

4. The system for intervertebral implantation according to claim 2 wherein said orifices have a circular or rounded section.

5. The system for intervertebral implantation according to claim 2 wherein said orifices have a tronco-conical outer segment that facilitates the relative motion between said clamp and said intersomatic cage.

6. The system for intervertebral implantation according to claim 1, wherein said cage further comprises toothing on each of said vertebral facing sides, wherein said toothing has a curved and parallel shape on each of said sides.

7. The system for intervertebral implantation according to claim 1, wherein said cage further comprises toothing on each of said vertebral facing sides, wherein said toothing has a straight and parallel shape on each of said sides.

8. The system according to claim 1, wherein a relative sliding of the clamp arms produces a positional rotation of the intersomatic cage held by the clamp.

9. The system according to claim 1, wherein said clamp further comprises a shaft threaded on one of the ends of the clamp, wherein said shaft regulates the sliding motion of the clamp arms, and wherein said shaft, on its opposite end comprises an area for control and actuation of said sliding motion, and wherein said shaft comprises, in an intermediate position, a recessed area in which is coupled the other clamp arm, this arm having a slanted shape that facilitates opening and closing the clamp arms while maintaining the interconnection with the sliding control of said clamp arms.

10. The system according to claim 1, wherein said copying element has positional regulation through a screw that adjusts its position to that of the attachment of the intersomatic cage.

11. The system according to claim 1, wherein said cam hinged to said copying element is also constituted as a spring for opening and closing the clamp.

12. The system according to claim 1, wherein flexing the clamp will maintain the tightening of the intersomatic cage, even if the pressure exerted manually on the clamp arms is released.

13. The system according to claim 1, wherein the clamp design allows disassembling main elements of said clamp without the need for tools, facilitating their cleaning.

14. The system according to claim 1, wherein the system allows repositioning the intersomatic cage at any stage of a cage implantation process.

15. A procedure for holding an intersomatic cage using the system according to claim 1, said procedure comprising:
  adjusting the anterior ends of said clamp on corresponding orifice of said intersomatic cage;
  tightening the clamp arms, thereby firmly holding said intersomatic cage; and
  sliding the clamp arms against each other by a rear actuator, resulting in a hinged rotation of said intersomatic cage such that said rotation is reproduced by said copying element.

* * * * *